United States Patent
Sugiyama

(10) Patent No.: US 7,754,149 B2
(45) Date of Patent: Jul. 13, 2010

(54) CLINICAL LABORATORY MANAGEMENT SYSTEMS, MANAGEMENT APPARATUSES, AND RECORDING MEDIA

(75) Inventor: Tomomi Sugiyama, Kobe (JP)

(73) Assignee: Sysmex Corporation, Kobe (JP)

( * ) Notice: Subject to any disclaimer, the term of this patent is extended or adjusted under 35 U.S.C. 154(b) by 1290 days.

(21) Appl. No.: 10/735,271

(22) Filed: Dec. 12, 2003

(65) Prior Publication Data

US 2005/0131734 A1 Jun. 16, 2005

(51) Int. Cl.
*G01N 35/00* (2006.01)
*G06F 19/00* (2006.01)

(52) U.S. Cl. .............. 422/67; 422/63; 436/43; 436/50; 702/19; 702/22; 340/500

(58) Field of Classification Search .............. 422/63–67; 436/43, 47, 49; 700/266
See application file for complete search history.

(56) References Cited

U.S. PATENT DOCUMENTS

| | | | |
|---|---|---|---|
| 5,077,666 A | 12/1991 | Brimm et al. | |
| 5,171,977 A | 12/1992 | Morrison | |
| 5,298,424 A * | 3/1994 | Shinohara | 436/43 |
| 5,814,276 A | 9/1998 | Riggs | |
| 6,275,150 B1 * | 8/2001 | Mandler et al. | 340/525 |
| 2005/0102166 A1 * | 5/2005 | Tohma | 705/3 |
| 2007/0038406 A1 * | 2/2007 | Uemura et al. | 702/127 |

FOREIGN PATENT DOCUMENTS

| | | |
|---|---|---|
| EP | 1107159 A2 * | 11/2000 |
| JP | H04-295764 | 10/1992 |
| JP | 2000-321281 | 11/2000 |

* cited by examiner

*Primary Examiner*—P. Kathryn Wright
(74) *Attorney, Agent, or Firm*—Brinks Hofer Gilson & Lione

(57) ABSTRACT

A clinical laboratory management system is described that includes an analyzer for analyzing a sample, and a management apparatus connected to the analyzer. The management apparatus includes (a) a storage configured for storing a result of an assay output from the analyzer, analyzer identification information for identifying whether or not the analyzer used for the assay has a dilution mode, and diluted sample identification information for identifying whether or not the sample used in the assay is a diluted sample; and (b) a controller configured for correcting the result when the analyzer used in the assay does not have a dilution mode, and the sample used in the assay is a diluted sample. Management apparatuses and recording media are also described.

16 Claims, 7 Drawing Sheets

| | Reception No. | Patient name | Patient ID | Rush | Assay item | Sample/Analyzer codes |
|---|---|---|---|---|---|---|
| Individual record { | 110001 | Toa Taroh | TT0019 | — | TP/GPT/G | B1/ME-1 |
| | 110002 | Toa Taroh | TT0019 | — | Urine(RBC | U2/ME-3 |
| | 110009 | Toa Jiro | TJ0002 | — | Na/K/Cl/Ca | B1/ME-1 |
| | 211001 | Toa Jiro | TJ0002 | — | Protein/Uro | U1/ME-4 |
| | 211004 | Toa Hanak | TH0001 | Rush | WBC | H1/ME-2 |
| | ... | | ... | | | |

CLINICAL LABORATORY MANAGEMENT SYSTEMS, MANAGEMENT APPARATUSES, AND RECORDING MEDIA

FIELD OF THE INVENTION

The present invention relates to clinical laboratory management systems, and more specifically, to clinical laboratory management systems for managing assay results from analyzers and various examination work and operations in medical facilities such as hospitals.

BACKGROUND

In recent years, clinical laboratory management systems for collectively managing various types of clinical laboratory work have become widely used in medical treatment facilities, such as hospitals. Such systems perform managed examination operations, such as examination scheduling, examination reception, printing barcode labels for adherence to sample containers such as blood collection vials and the like, printing work sheets such as examination sequence guidelines, transporting samples to the laboratory, assays using various analyzers, assay result tabulation, validation (confirmation of assay results), re-examination instructions, assay result reports, and the like.

Such clinical laboratory management systems are formed using a server computer as the basis of the system, to which input/output terminals in the form of client computers are connected over a network. Furthermore, analyzers connected to this system automatically input an assay result obtained by assaying a sample to the system over the network, and this result is ultimately reported to the party who originally requested the examination.

There may be times when a sample, such as blood (e.g., whole blood, serum, plasma), urine or the like is examined using an analyzer, and the fluid volume of the sample is not the minimum volume required for measurement by the analyzer. For example, there may be times when a sufficient quantity of sample cannot be collected from a patient because the patient is an infant, when a sample must be apportioned in accordance with the number of examinations to be performed, and when a sample which has already been assayed once requires re-examination. At such times, when a supplementary sample cannot be collected, the assay may be performed after diluting the sample to a predetermined degree. First, the sample is diluted by increasing the fluid volume so as to be sufficient for the assay (dilute sample preparation). Then, the sample is assayed using the same analyzer as used for an undiluted sample (normal sample). Subsequently, the result of the assay is corrected based on the degree of dilution, and the corrected result is used as the final assay result.

In recent years, analyzers capable of assay mode selection, which perform assays by selecting between a normal mode for assaying normal samples and a dilution mode for assaying dilute samples, have been used to improve analyzer functionality. When performing an assay in the normal mode, the assay is performed using a normal sample which is not diluted, and the obtained assay result is output. However, when performing an assay in the dilution mode, a dilute sample is prepared by diluting a sample to a predetermined degree and performing the assay. The analyzer then corrects the obtained assay result based on a predetermined degree of dilution stored in memory beforehand, and this corrected assay result is output as the final assay result. If this analyzer is connected to the system, the assay result is automatically input to the system (online input).

When a dilute sample is assayed using an analyzer which does not have a dilution mode and the assay result is input to the clinical laboratory management system, the assay result is not automatically input from the analyzer to the system (online input), but rather is input by the following procedure. First, the assay is performed using an analyzer. Then, a laboratory technician performs corrective calculations on the assay result. The corrected result is then manually input (offline input) to the system from an input terminal as the final assay result. When the result of a dilute sample assay is automatically input directly from an analyzer to the system (online input), the uncorrected result of the assayed dilute sample is undistinguished from an assay result of a normal sample, such that the sample may be perceived as an abnormal assay result even if the sample is collected from a healthy patient.

When an analyzer without a dilution mode is connected to a system in this way, the assay result cannot be input to the system via online input when a dilute sample is assayed. When normal samples and dilute samples are mixed among the samples to be assayed, various disadvantages arise inasmuch as the assay results of the samples cannot be input online, the normal samples and dilute samples must be separated before performing the assay, thereby complicating the examination operation and reducing work efficiency. Although these problems can be resolved if all the analyzers connected to the system are provided with a dilution mode, such an arrangement would limit the types of analyzers which could be connected to the system, thereby restricting design freedom when constructing or expanding the system.

In terms of advancing clinical examination operations by allowing the mixed use of normal samples and dilute samples, it is desirable that operation efficiency is improved so as to prevent mishandling of samples, and to allow easier handling of complex samples, such as preparing dilute samples and the like.

SUMMARY

The scope of the present invention is defined solely by the appended claims, and is not affected to any degree by the statements within this summary.

A first clinical laboratory management system embodying features of the present invention includes: an analyzer for analyzing a sample, and a management apparatus connected to the analyzer. The management apparatus includes (a) a storage means for storing a result of an assay output from the analyzer, analyzer identification information for identifying whether or not the analyzer used for the assay has a dilution mode, and diluted sample identification information for identifying whether or not the sample used in the assay is a diluted sample; and (b) a control means for correcting the result when the analyzer used in the assay does not have a dilution mode, and the sample used in the assay is a diluted sample.

A second clinical laboratory management system for managing an assay result acquired by an analyzer, which embodies features of the present invention, includes: (a) an examination information storing means for storing examination information relating to a clinical examination; (b) a required fluid quantity determining means for determining a quantity of fluid sample required for an assay by the analyzer based on the examination information stored by the examination information storing means; (c) a sample fluid quantity input means for inputting a sample fluid quantity prepared for the assay by the analyzer; (d) a dilution rate calculating means for calculating a dilution rate based on the sample fluid quantity input by the sample fluid quantity input means and the quantity of fluid sample required for the assay determined by the required fluid quantity determining means; (e) an assay result receiving means for receiving an assay result from the analyzer which has assayed a diluted sample based on the dilution rate calculated by the dilution rate calculation means; and (f) an assay result correcting means for correcting the assay result received by the assay result receiving means based on the dilution rate calculated by the dilution rate calculating means.

A third clinical laboratory management system for managing an assay result acquired by an analyzer, which embodies features of the present invention, includes: (a) an examination information storing means for storing examination information relating to a clinical examination; (b) a required fluid quantity determining means for determining a quantity of fluid sample required for an assay by the analyzer based on the examination information stored in the examination information storing means; (c) a sample fluid quantity input means for inputting a sample fluid quantity prepared for the assay by the analyzer; (d) a dilution rate calculating means for calculating a dilution rate based on the sample fluid quantity input by the sample fluid quantity input means and the quantity of fluid sample required for the assay determined by the required fluid quantity determining means; and (e) a dilution rate output means for outputting the dilution rate calculated by the dilution rate calculating means together with sample identification information.

A management apparatus for managing an analyzer, which embodies features of the present invention, includes: (a) a storage means for storing a result of an assay output from the analyzer, analyzer identification information for identifying whether or not the analyzer used for the assay has a dilution mode, and diluted sample identification information for identifying whether or not a sample used in the assay is a diluted sample; and (b) a control means for correcting the result when the analyzer used in the assay does not have a dilution mode, and the sample used in the assay is a diluted sample.

A first recording medium embodying features of the present invention includes a computer program for execution by a management apparatus connected to an analyzer, in which the program includes: (a) a function for storing a result of an assay output from the analyzer, analyzer identification information for identifying whether or not the analyzer used for an assay has a dilution mode, and diluted sample identification information for identifying whether or not a sample used in the assay is a diluted sample; and (b) a function for correcting the result when the analyzer used in the assay does not have a dilution mode, and the sample used in the assay is a diluted sample.

A second recording medium embodying features of the present invention includes a computer program for execution by a management apparatus connected to an analyzer, in which the program includes: (a) a function for storing examination information relating to a clinical examination; (b) a function for determining a quantity of fluid sample required for an assay by the analyzer based on examination information that is stored; (c) a function for inputting a sample fluid quantity prepared for the assay by the analyzer; (d) a function for calculating a dilution rate based on the sample fluid quantity and the quantity of fluid sample required for the assay; and (e) a function for receiving an assay result from the analyzer which has assayed a diluted sample based on the dilution rate that is calculated.

In accordance with the present invention, analyzers having a dilution mode and analyzers without a dilution mode can be connected to a clinical laboratory management system, and online input can be achieved without distinguishing between assay results of dilute samples and assay results of normal samples from each analyzer. Furthermore, sample handling and dilution operations and the like are easily accomplished, thereby minimizing or preventing sample handling errors.

BRIEF DESCRIPTION OF THE DRAWINGS

FIG. 2 illustrates the table of the examination information database of a clinical laboratory management system.

FIG. 3 illustrates the arrival confirmation input screen of a clinical laboratory management system.

DETAILED DESCRIPTION

Figure 1:
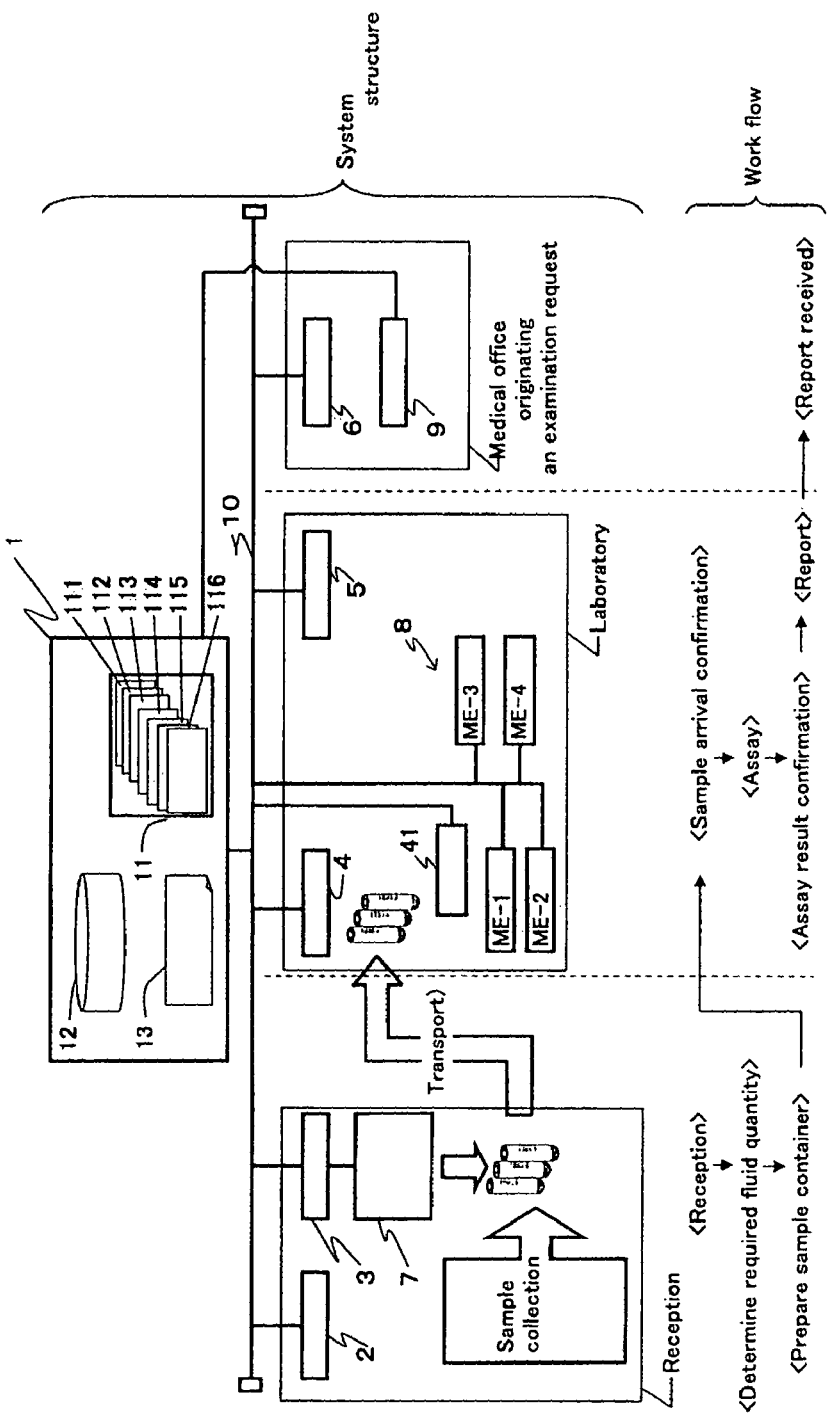
FIG. 1 illustrates the hardware structure of a clinical laboratory management system and the clinical examination work flow.

Presently preferred embodiments of clinical laboratory management systems embodying features of the present invention are described hereinafter. FIG. 1 shows the relationship between the various clinical examination operations and the structure of the clinical laboratory management system and peripheral devices. In this system, a server 1 and other peripheral devices—clients 2, 3, 4, 5, and 6, sample container supply device 7, analyzer group 8 (ME-1, ME-2, ME-3, ME-4), label printer 41, and FAX 9—are connected via a local area network (LAN) 10.

Figure 7:
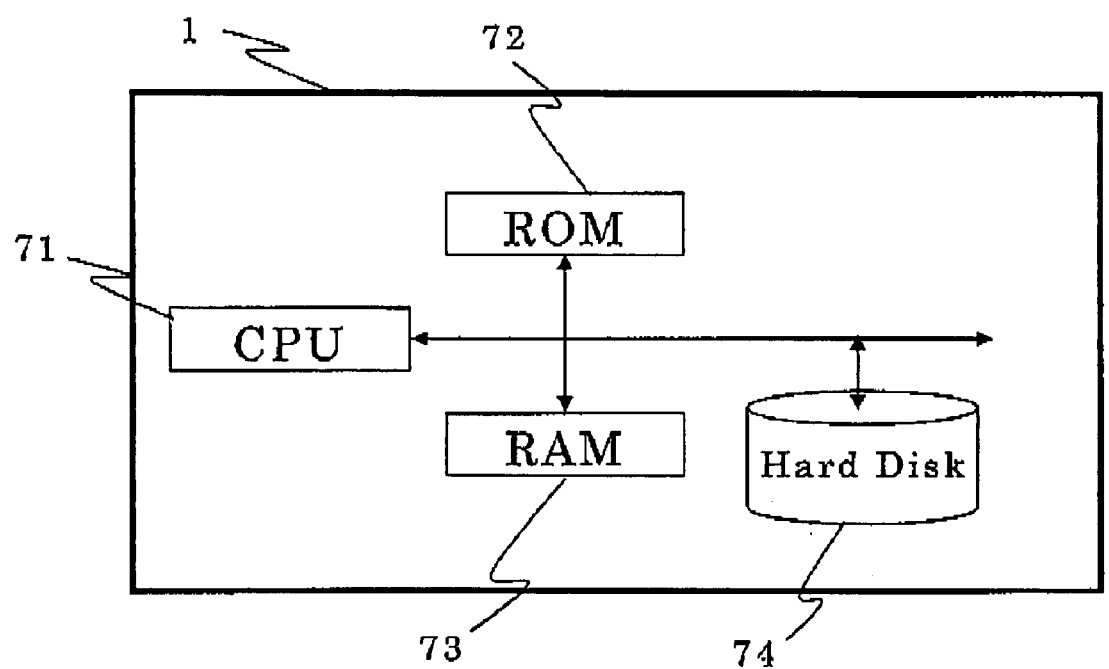
FIG. 7 illustrates a configuration of a server.

The server 1 and clients 2, 3, 4, 5, and 6 are all general purpose computers provided with a CPU 71, ROM 72, RAM 73, hard disk 74, and the like, as shown in FIG. 7, and each is further provided with input devices such as a keyboard, mouse, and the like, and a display device such as a CRT, LCD, and the like. Each client functions as an input/output terminal for various types of input and output in the clinical laboratory management system, and transmits and receives information to and from the server 1. When any type of device is connected to a client, information is transmitted and received between the client and the connected device.

The sever 1 stores and manages an application program 11 for making the clients function as an input/output terminal, receiving information, and performing information processing such as storing and output based on the received information.

The server 1 functions as an input/output terminal similar to the clients, and receives information transmitted from the clients and analyzers, and stores and manages an application program 11 for performing information processing such as storing and output based on the received information. Each client realizes various types of functions as an input/output terminal by reading the application program 11 for managing of the server 1 as necessary. The application program 11 is a set of a plurality of program modules, among which are included a required fluid quantity calculating module 111, a sample fluid quantity input module 112, a dilution rate calculating module 113, an assay result receiving module 114, a correction determining module 115, and an assay result correcting module 116. These modules are further described below.

Furthermore, the server 1 manages an examination information database 12. The examination information database 12 stores various information (e.g., examination information)

relating to clinical examinations for each examination managed by the system. The examination information includes patient attribute information and analyzer used, assay item, assay result, sample identification information for identifying each sample, and the like. The information stored in the examination information database 12 is input from the clients and analyzers in the clinical examination operations (which include sample reception, sample arrival confirmation, assay, assay result confirmation, report preparation, report output, and the like, and are described below) performed through the clients and analyzers. The reception of this input and the storage of the examination information in the examination information database 12 are executed by the previously described application program 11.

The server 1 manages a sample quantity master file 13. The sample quantity master file 13 records the suction quantity for each assay item, dead volume of the sample container used, and calculation method for calculating the required fluid quantity for the combined assays for each analyzer connected to the system.

The suction quantity is the quantity of fluid suctioned by the analyzer for an assay. The dead volume is the unsuctionable quantity of fluid remaining in the bottom of the sample container, and differs according to the size and shape of the sample container and the suction mechanism of the analyzer. Although the dead volume portion of a sample is not actually suctioned by the analyzer and used in analysis, the analyzer cannot suction a proper quantity of a sample when there is no sample dead volume present in the sample container, such that an assay cannot be performed. Therefore, the fluid quantity required for an assay (required fluid quantity) is calculated in terms of the suction quantity and dead volume.

The required fluid quantity is the total of the suction quantity and the dead volume, and is a fluid quantity of the minimum amount of sample required to be put into the sample container so that the analyzer can perform an assay. Using the analyzer ME-1 (biochemical analyzer, serum sample) in an illustrative example, the suction quantity of the serum sample required for TP assay is 0.2 ml, the suction quantity of the serum sample required for GPT assay is 0.2 ml, the suction quantity of the serum sample required for GOT assay is 0.2 ml, the suction quantity of the serum sample required for γ-GTP assay is 0.2 ml, and the dead volume of the sample container used in this analyzer is 0.2 ml. The suction quantity of each assay item and the dead volume are recorded in the sample quantity master file 13.

Since the method of calculating the required fluid quantity is to calculate the required fluid quantity according to the combination of the assay items of the assay request, the rule is to combine in some way the input suction quantities and the dead volume. In the analyzer ME-1, for example, the calculation method when the assay request includes a single item is described below.

The required fluid quantity is the dead volume added to the suction volume required to assay the single assay item. Furthermore, the calculation method when the assay request includes a plurality of assay items is described below.

The required fluid quantity is the dead volume added to the suction volume required to assay each of the assay items.

This calculation method is recorded in the sample quantity master file 13.

Combined assay items and the value of the dead volume and the like differ according to the type of analyzer and method used to calculate the required fluid quantity. Therefore, the recording of the sample quantity master file is performed for every analyzer when there is a plurality of different types of analyzers, and when the analyzer settings are changed even for identical analyzers. The sample quantity master record input operation and storage in the sample quantity master file 13 are realized by the operation of the application program 11. The sample quantity master record input operation can be performed from the server 1 and each of the clients.

The chain of operations in the clinical examination managed by the system are described below. In this system, the chain of operations of the clinical examinations include "reception," "required fluid quantity calculation," "sample container preparation," "sample arrival confirmation," "assay," "assay result confirmation," and "reporting." When each operation ends, the examination information from each analyzer and client used in the operation is input and stored in the examination information database 12.

Reception

When a physician determines that an examination is required for a patient, the medical office requests the examination. An order with the patient name, examination items, and the like is received and recorded. The chain of examination operations begins in the clinical laboratory management system in this way. The reception input is accomplished by an technician using an input device such as a mouse, keyboard or the like on a reception input screen displayed on the display device of the client 2. The reception time and the input content are stored in the examination information database 12 managed by the server 1.

FIG. 2 shows the table of the examination information database 12. Records are prepared for each received examination, and examination information, including the "reception number," "patient name," "patient ID," "rush examination status," "examination item," and "sample and analyzer specification codes" for specifying the type of sample and analyzer used are input and stored in the examination information database 12 at the time of reception. Furthermore, the time at which the reception is input is also stored.

Required Fluid Quantity Determination

When the order is received, the required fluid quantity calculating module 111 calculates the required fluid quantity of the sample for this assay based on the calculation method in the sample quantity master file 13 and the information in the examination information database 12 for the assay item and the analyzer used for the assay. If the suction quantity of the serum sample required for a TP assay is designated as A, the suction quantity of the serum sample required for a GPT assay is designated as B, the suction quantity of the serum sample required for a GOT assay is designated as C, the suction quantity of the serum sample required for a γ-GTP assay is designated as D, and the dead volume of the sample container used in the analyzer is designated as E, then, in accordance with the method for calculating the required fluid quantity in the analyzer ME-1, the required fluid quantity for a TP assay is A+E. When GOT and γ-GTP assays are performed, the required fluid quantity is C+D+E. When TP, GPT, GOT and γ-GTP assays are performed, the required fluid quantity is A+B+C+D+E. In this case, since A=0.2 ml, B=0.2 ml, C=0.2 ml, D=0.2 ml, and E=0.2 ml, when these values are substituted in the equations, the required fluid quantity for the combined assay items can be calculated. In the case of the equations above, A+E=0.4 ml, C+D+E=0.6 ml, and A+B+C+D+E=1.0 ml, such that the following values are obtained: when assaying TP, the required fluid quantity is 0.4 ml; when assaying GOT and γ-GTP, the required fluid quantity is 0.6 ml; and when assaying TP, GPT, GOT, and γ-GTP, the required fluid quantity is 1.0 ml.

The calculated required fluid quantities are stored in the examination information database 12.

Sample Container Preparation

Figure 5:
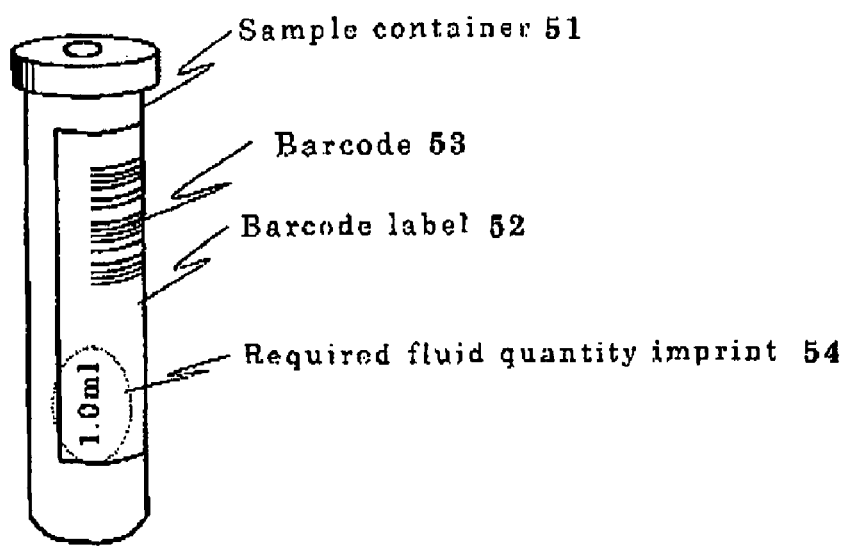
FIG. 5 illustrates a barcode label printed by a clinical laboratory management system.

When the required fluid quantity is recorded in the examination information database 12, information, which includes the examination required fluid quantity, patient attribute information, analyzer used, examination item and the like, is transmitted from the server 1 to the examination container supply device 7 through the client 3. The examination container supply device 7 accommodates a plurality of types of examination containers for collecting samples, and selects and supplies the type and number of sample containers in accordance with the received examination information. Furthermore, the examination container supply device 7 is provided with a built-in label printer, and prints a barcode label, which includes various types of information such as patient information, examination date, reception number, sample container ID, type of analyzer used, and information identifying the sample in accordance with the examination information received from the server 1, and automatically adheres this barcode label on the selected sample container. Then, sample container supply device 7 supplies the sample container in accordance with the examination content. As shown in FIG. 5, a barcode 53 and the required fluid quantity 54 for the assay to be performed using the sample accommodated in the sample container 51 are printed on the label 52 adhered to the sample container 51.

Sample Arrival Confirmation

The sample container accommodating the sample is transported to a laboratory, such as the blood examination room or the urine examination room. In FIG. 1, a plurality of examination rooms are represented as a single laboratory. When the sample collected from the patient arrives at the laboratory, a sample arrival confirmation is input. The inputting of the sample arrival confirmation is accomplished by reading the barcode label adhered to the sample container using a barcode reader (not shown) of the client 4 installed in the laboratory. When the barcode is unreadable by the barcode reader due to soiling of the barcode or the like, it is possible to input the confirmation on a predetermined sample arrival confirmation input screen displayed on the display device of the client 4 using an input device, such as a mouse, keyboard or the like. When the sample arrival confirmation is input, the moment the sample arrival confirmation is input is stored in the examination information database 12 managed by the server 1.

Figure 3:
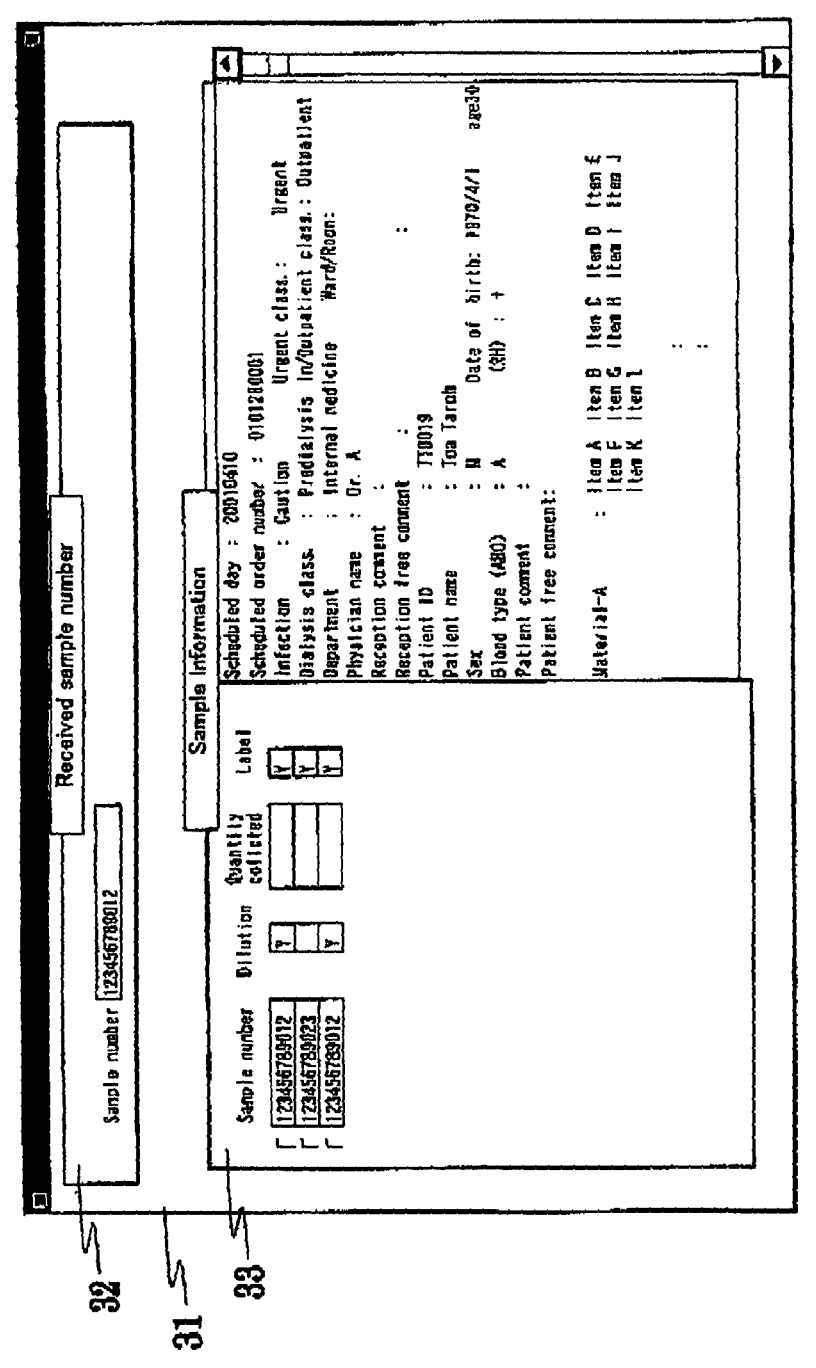

FIG. 3 shows an example of the arrival confirmation input screen 31. A field for the "received sample number" 32 of the delivered sample is provided in the upper part of the screen, and the sample number of the most recently read barcode is displayed. Below the "received sample number" field 32 is provided a "sample information" field 33. In the sample information field 33, detailed information such as patient attribute information, examination item and the like relating to the sample displayed in the "received sample number" field 32 is displayed on the right side. Also, on the left side in the "sample information" field 33 is displayed a list of the sample numbers read by the barcode reader. This list is displayed in descending order with the latest information at the top. Information on three samples is displayed in this example.

In the arrival confirmation input screen shown in the drawing, whether or not dilution of the sample is necessary can be input via the arrival confirmation input. When the sample arrives at the laboratory and a clinical technician determines that the fluid quantity of the sample (hereinafter referred to as "sample fluid quantity") needed for each assay by an analyzer does not match the required fluid quantity printed on the label of the sample container, the technician inputs instructions that the sample should be assayed after the sample has been diluted (hereinafter referred to as "dilution-requiring sample"). The input of instructions that this sample is a dilution-requiring sample is accomplished by inputting [Y] in the "dilution" column provided adjacent to the list of displayed sample numbers in the "sample information" field.

In regard to a sample which has been designated a dilution-requiring sample, the sample fluid quantity is input in the "collection quantity" column. If a special operation is not required regarding input of a sample fluid quantity, then nothing is displayed in the "collection quantity" column, and the initially set fluid quantity is automatically input in the system and stored in the examination information database 12. However, when a technician inputs an optional numeric value in the "collection quantity" column, that numeric value is substituted for the sample fluid quantity rather than the initially set value, and stored in the examination information database 12.

For example, when a sample collected from a specific patient is subjected to TP, GPT, GOT, and γ-GTP assays using the analyzer ME-1, the required fluid quantity is 1.0 ml in view of the calculation method used in the example, and this value is printed on the label adhered to the sample container. If the technician determines that a sample fluid quantity of 1.0 ml is insufficient and that dilution is required, the technician inputs instructions that this sample is a dilution-requiring sample. Then, an initial set value (in this example, 0.5 ml) is input as the sample fluid quantity. When it is determined that the sample quantity is equal to or greater than 0.5 ml, this initial value may be used. When the sample fluid quantity is at least 0.5 ml or more, a sample fluid quantity of 0.5 ml is input in accordance with the initial set value. When it is determined that the sample fluid quantity is less than 0.5 ml, at the least, the sample fluid quantity accommodated in the container is input as the fluid quantity.

The input of instructions that the sample is a dilution-requiring sample, and the input of the sample fluid quantity are respectively recorded in the examination information database 12. A screen for receiving the input of the sample fluid quantity is output to the display device of the client 4, and the input content from the client 4 is stored in the examination information database 12. This procedure is based on the sample quantity input module 112.

Regarding examinations for which instructions specifying the sample as a dilution-requiring sample are recorded in the examination information database 12, the dilution rate calculating module 113 obtains the sample fluid quantity and the required fluid quantity for the specific assay from the examination information database 12. Then, the dilution rate is calculated by dividing the required fluid quantity by the sample fluid quantity. In the description below, the same example as above is used, wherein the sample is subjected to TP, GPT, GOT, and γ-GTP assays using the analyzer ME-1. In this instance, the required fluid quantity of 1.0 ml is stored in the examination information database 12. When the stored fluid quantity of the sample is 0.5 ml, the dilution rate calculating module 113 obtains the value of [1.0 ml] as the required fluid quantity, and the value [0.5 ml] as the sample fluid quantity from the examination information database 12. Then, a dilution rate of two-fold (2×) is calculated by dividing the required fluid quantity by the sample fluid quantity. The calculated dilution rate is stored in the examination information database 12, and displayed on the display device of the client 4.

Figure 6:
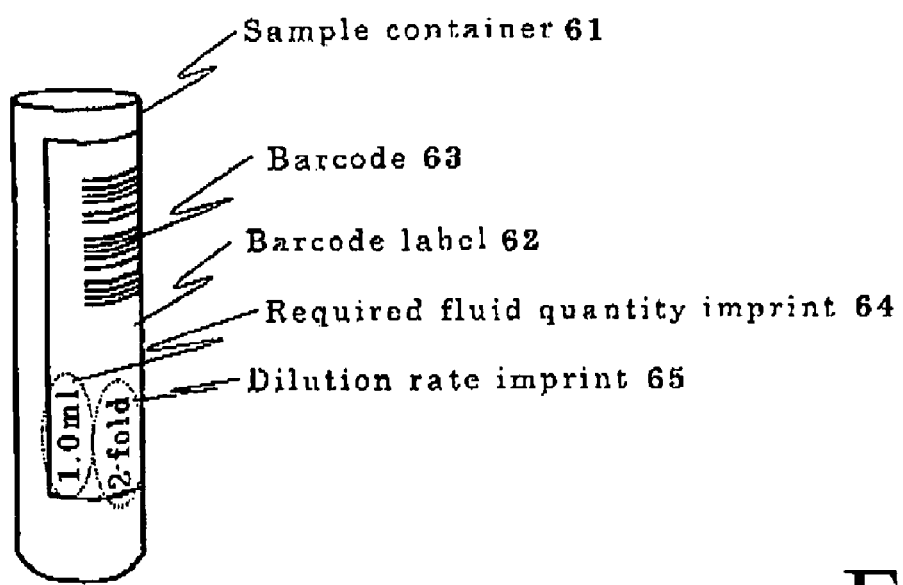
FIG. 6 illustrates a barcode label printed by a clinical laboratory management system.

Furthermore, when an input instruction indicating that printing is required is entered in the label printing input column (i.e., the column marked "label") in the arrival confirmation input screen, the server 1 outputs sample identification information and dilution rate information to the label printer 41. In this way, a printed label bearing the dilution rate calculated by the dilution rate calculating module 113 is printed by the label printer 41. This label is adhered to the sample container which accommodates the prepared dilution sample so as to be supplied to the analyzer. FIG. 6 shows a sample container 61 with this label 62 adhered. Printed on this label are the dilution rate 65 calculated by the dilution rate calculating module 113, the required fluid quantity 64, and a barcode 63, which includes patient information, examination date, reception number, sample container ID, type of analyzer used, sample identification information, and the like. The technician prepares the dilute sample by diluting this sample with a predetermined dilution fluid based on the dilution rate displayed on the display device of the client 4 and the dilution rate 65 printed on the label 62 adhered to the sample container 61 used for this dilute sample. The recording of the dilution rate calculated as described above in the examination information database 12 is executed by the operation of the dilution rate calculating module 113. The input/output of the server 1 and the other peripheral devices (e.g., label printing output and the like) are executed by the operation of the application program 11.

Assay

The sample for which arrival has been confirmed is set in the analyzer and the requested examination items are assayed. Among the analyzers ME-1, ME-2, ME-3, and ME-4 included in the analyzer group 8, ME-1 is a biochemical analyzer for assaying biochemical components contained in blood. ME-2 is a blood analyzer for assaying the number of erythrocytes, leukocytes, platelets, and hemoglobin concentration in the blood. ME-3 and ME-4 are urine analyzers. ME-3 is a urine analyzer for assaying tangible components in the urine, such as erythrocytes, leukocytes, bacteria, and casts, and is used for so-called urine sediment analysis. ME-4 is a urine analyzer for assaying chemical components in the urine, such as protein, glucose, and occult blood, and is used for so-called urine qualitative analysis. Any of the analyzers included in the analyzer group 8 can read the barcode adhered to the sample container so as to completely automate the assay of the requested examination item.

The analyzers ME-1, ME-2, ME-3, and ME-4 are respectively connected to the network and the server 1, and when the assay ends in each analyzer, the assay result and the information of the reception number, sample container ID, and assay date and time are automatically transmitted and input in the server 1. The analyzer ME-1 is not provided with a dilution mode, and cannot perform a correction calculation on the assay result output to the server 1 based on the dilution rate. The analyzers ME-2, ME-3, and ME-4 are provided with a dilution mode, and when a dilute sample is assayed, these analyzers output to the server 1 an assay result which has been corrected based on the dilution rate. The assay result output from the analyzers are received by the server 1 by means of the operation of the assay result receiving module 114, and the assay result is then stored in the examination information database 12.

The assay result stored in the examination information database 12 is examined by the correction determining module 115 to identify whether or not the sample was assayed by an analyzer provided with a dilution mode. Assay results identified as coming from an analyzer that is not provided with a dilution mode are examined by the correction determining module 115 to identify whether or not the assay was performed using a normal sample or a dilute sample. This identification is performed based on the examination information stored in the examination information database 12. When the assay result has been received from the analyzer ME-1 and the sample assayed is a dilute sample, an assay result correcting module described below determines that correction is necessary. When the assay result has been received from the analyzer ME-1 and the sample assayed is a normal sample, and when the assay result is received from any of the analyzers ME-2, ME-3, and ME-4, the assay result correcting module 116 described below determines that correction is unnecessary.

For assay results determined to require correction by the assay result correcting module 116 (results of assays performed using a dilute sample by an analyzer which is not provided with a dilution mode), the assay result correcting module 116 obtains the assay result and the dilution rate from the examination information database 12. Then, the assay result is corrected based on the dilution rate, and a corrected assay result is calculated. As previously described, the analyzer ME-1 is not provided with a dilution mode, and in the cited example, the sample stored in the examination information database 12 has a sample fluid quantity of 0.5 ml, such that the calculated corrected result respectively doubles the assay result value for the TP, GPT, GOT, and γ-GTP assays because the dilution rate is calculated as two-fold [2×]. The corrected result calculated in this way is stored in the examination information database 12. The results of assays performed using normal samples are recorded in the examination information database 12 directly without correcting the assay result for both assay results from analyzers which are provided with a dilution mode and assay results from analyzer which are not provided with a dilution mode.

As described above, the determination as to whether or not correction is required for the assay result of a dilute sample is executed by the operation of the correction determining module 115. Furthermore, the recording of the correction calculation and the corrected assay result in the examination information database 12 is executed by the assay result correcting module 116. Thus, the correction determining module 115 identifies whether or not the assay result was assayed by an analyzer provided with a dilution mode, and when the analyzer is not provided with a dilution mode, identifies whether or not the assayed sample was a normal sample or a dilute sample, so as to determine whether or not the correction calculation is necessary. Then, for the assay results which have been determined to require a correction calculation, the assay result correcting module 116 calculates the correction using the dilution rate. In this way, analyzers can be connected to this system regardless of whether or not these analyzers have a dilution mode, and even the results of assayed dilute samples can be input online.

Validation

Validation confirms that a specific assay result (a corrected assay result in the case of assays of dilute samples) may be reported as an official assay result to the point of origin of the examination request. Validation input is accomplished by selecting an assay result which is the object of validation (a corrected assay result in the case of assays of dilute samples) on a predetermined validation screen output to the display device of the client 5. The validated item is stored in the examination information database 12 with the time of validation input.

Reports

When the validation of the assay result ends, an assay report is prepared and transmitted from the laboratory to the medical office that originally requested the examination. Report preparation is accomplished by the technician inputting the necessary items on a predetermined report preparation screen displayed on the display device of the client 5 using an input device, such as a mouse, keyboard or the like.

When the report preparation ends, the data of the prepared report are transmitted to the server 1, and stored in the server 1 associated with the examination information records stored in the examination information database 12. These data are transmitted from the server 1 to the FAX 9 via a FAX modem (not shown). The FAX 9 is disposed in the medical office originally requesting the examination, and prints out the data of the received report. When the information transmission from the server 1 to the FAX 9 ends, the time the transmission ends is stored in the examination information database 12. The data of the report stored on the server 1 can be viewed on a predetermined report access screen displayed on the display device of the client 6 disposed in the medical office originally requesting the examination.

Information Processing Flow

Figure 4:
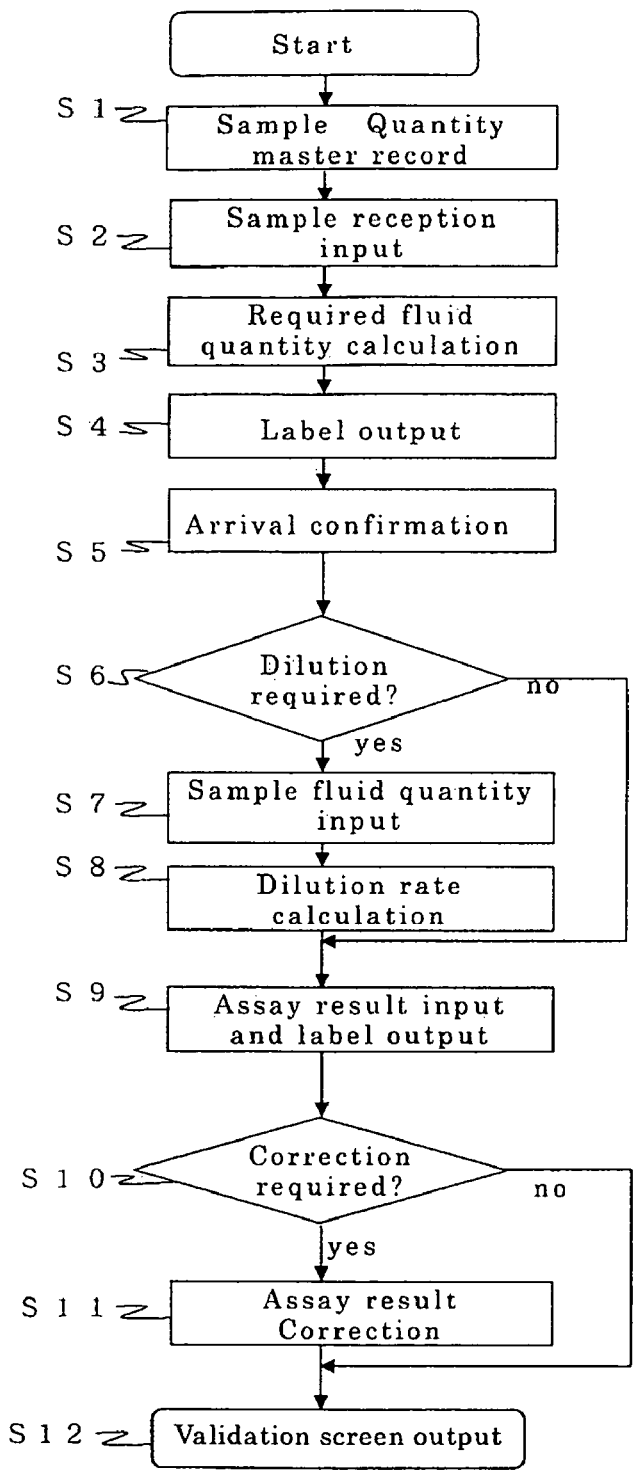
FIG. 4 illustrates the information processing flow of a clinical laboratory management system.

The information processing flow of the application program 11 performing an assay from the sample quantity master record to the output of the validation screen is described below with reference to FIG. 4.

S1: The master record screen of the predetermined sample quantity master record is displayed on any of the display devices of the server 1 or the clients, and the technician requests the sample quantity master record. When the method for calculating the required fluid quantity and the like are input in accordance with the request, the requested content is recorded in the sample quantity master file 13. Then, the routine moves to S2.

S2: Input examination information is stored in the examination information database 12 based on the assay reception input. Then, the routine moves to S3.

S3: The required fluid quantity calculating module 111 obtains information related to the assay items and the analyzer used for the received examination from the examination information database 12, and calculates the required fluid quantity using the calculation method for the required fluid quantity recorded in the sample quantity master file 13. Then, the calculated required fluid quantity is stored in the examination information database 12. Then, the routine moves to S4.

S4: The calculated required fluid quantity is compiled together with the examination information such as the examination date, patient name, and the like, and transmitted to the sample container supply device 7, and a barcode label is printed. Then, the routine moves to S5.

S5: A predetermined arrival confirmation screen is displayed on the display device of the client 4, and the technician is requested to input the arrival confirmation. When the confirmation is input in response to the request, the arrival confirmation input is stored in the examination information database 12. Then, the routine moves to S6.

S6: Input as to whether or not dilution is necessary is requested in the arrival confirmation screen. When the technician inputs that dilution is required, the routine moves to S7. When the technician inputs that dilution is not required, the routine moves to S9.

S7: The sample fluid quantity input module 112 receives the input sample fluid quantity in the arrival confirmation screen. When the sample fluid quantity is entered by the technician or by the initial set value, this sample fluid quantity is stored in the examination information database 12. Then, the routine moves to S8.

S8: The dilution rate calculating module 112 obtains the sample fluid quantity and the required fluid quantity from the examination information database 12, and calculates the dilution rate by dividing the required fluid quantity by the sample fluid quantity. Then, the calculated dilution rate is stored in the examination information database 12. When necessary, the dilution rate is output for printing of a label. Then, the routine moves to S9.

S9: The assay result receiving module 114 receives and inputs the assay result output from the analyzer, and stores the information in the examination information database 12. Then, the routine moves to S10.

S10: The correction determining module 115 determines whether or not the assay result stored in the examination information database 12 requires correction based on the dilution rate, and makes this determination based on the examination information stored in the examination information database 12. When the determination result is that correction is required, the routine moves to S11. When correction is not required, the routine moves to S12.

S11: The assay result correcting module 116 obtains the assay result and dilution rate from the examination information database 12, and corrects the assay result by multiplying the assay result by the dilution rate. The corrected assay result is stored in the examination information database 12. The dilution rate used in the correction is the value recorded in the examination information database 12.

S12: For an assay result determined not to require correction in S10, the assay result stored in the examination information database 12 in S9 is output to the validation input screen. For an assay result determined to require correction in S10, the corrected assay result stored in the examination information database 12 in S1 is output to the validation input screen.

When the four assays of TP, GPT, GOT, and γ-GTP are performed by the analyzer ME-1 (required fluid quantity 1.0 ml), the fluid quantity of 0.5 ml input as the sample fluid quantity is initially set in S7. When the technician determines that the sample fluid quantity is approximately 0.7 ml, the initially set value is used. Since the fluid quantity of the sample is equal to or greater than 0.5 ml, then according to the initially set value, a sample fluid quantity of 0.5 ml is automatically input. Then, when the sample is diluted, the dilute sample fluid quantity is 1.4 ml since the dilution rate is calculated as two-fold [2×] Although this value exceeds the value of 1.0 ml of the required fluid quantity, the fact that the fluid quantity required for a dilution result is exceeded is not a problem. According to this arrangement, the actual fluid quantity of the sample is in excess of that needed for the assay, thus simplifying the input of the sample fluid quantity for the technician. Even when the required dilute sample is less than 1.0 ml, medical facilities using this system will seldom send a sample less than 0.5 ml to the laboratory, which makes the setting at this level useful. The setting of the sample fluid quantity is not necessarily limited to the above example, and the numeric value of the setting may be modified according to factors such as the types of analyzers, types of assays, and combinations thereof at the medical facility using this system. The setting also may be multi-leveled.

In the above embodiment, when determining the required fluid quantity, the required fluid quantity determining module 111 calculates the required fluid quantity of a sample used in an assay based on the information of the assay item and analyzer used for the assay stored in the examination information database 12, and the calculation method stored in the sample quantity master file 13. However, this calculation may not necessarily be required. When all assay items can be combined in using a predetermined analyzer, the required fluid quantity may be determined by storing the required fluid quantity for each combination beforehand in the sample quantity master file 13, and selecting the required fluid quantity of the assay item combination from the sample quantity master file 13 based on the information stored in the examination information database 12.

In clinical laboratory management systems embodying features of the present invention, the assay result is corrected based on the dilution rate calculated from the required fluid quantity and the sample fluid quantity. This correction can be applied when the sample is a dilute sample and when it is a normal sample. Therefore, the processing flow of the clinical laboratory management system can be established without distinguishing between dilute samples and normal samples, and the examination operation is made more efficient. Furthermore, since a means is provided for determining whether or not an assay result requires correction, analyzers may be connected to the system and used regardless of whether or not they have a dilution mode.

In clinical laboratory management systems embodying features of the present invention, sample identification information and dilution rate are output together to a connected label printer so as to print a label bearing the sample identification information and dilution rate. Therefore, the work efficiency of clinical examinations is improved because the sample can be diluted after confirming the dilution rate of each sample when the printed label is adhered to a predetermined sample container. Furthermore, dilute samples can be identified at a glance from among a plurality of containers accommodating samples, thereby preventing mishandling of samples.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A clinical laboratory management system comprising:
   a first analyzer being of a type without a dilution mode for performing types of assays on a sample received in a quantity and given an analyzer specification code for identifying the analyzer and the type thereof;
   a second analyzer being of a type with a dilution mode for performing types of assays on a sample received in a quantity and given an analyzer specification code for identifying the analyzer and the type thereof; and
   a management apparatus connected to the first analyzer and the second analyzer, wherein the management apparatus comprises a computer and a memory which stores (a) a database which stores the analyzer specification code and requested assay information for identifying at least one requested type of assay to be performed on the sample, and (b) a master file which stores calculation methods for calculating required total sample quantities necessary for the analyzer to perform the types of assays individually and in combination,
   the memory also storing a plurality of program modules executable by the computer to:
   use the requested assay information stored in the database and one of the methods stored in the master file, which is selected by the computer in accordance with the requested assay information, to calculate, and store in the database, a required total quantity, which is a minimum sample quantity necessary for one analyzer to perform the at least one requested type of assay on the sample;
   receive, and store in the database, a dilution instruction for diluting the sample;
   respond to reception of the dilution instruction to divide the required total quantity stored in the database by the received quantity of the sample to calculate, and store in the database, a dilution rate of the sample;
   receive, and store in the database, an assay result of the sample from said one analyzer;
   respond to reception of the assay result to examine the analyzer specification code of said one analyzer stored in the database and determine whether the database stores the dilution instruction, in order to decide whether said one analyzer is of a type without a dilution mode and thus the assay result should be corrected; and
   when it is decided that said one analyzer is of a type without a dilution mode, and the assay result should be corrected, use the stored dilution rate from the database to correct the assay result with the dilution rate.

2. The clinical laboratory management system of claim 1, wherein the database further stores suction quantities required for the first and second analyzers to perform the respective types of assays.

3. The clinical laboratory management system of claim 2, wherein the management apparatus is connected to a terminal device for information input, and the computer displays a screen which invites an input of the received quantity of the sample.

4. The clinical laboratory management system of claim 2, wherein the received quantity of the sample is pre-stored in the database.

5. The clinical laboratory management system of claim 3, wherein the computer determines whether the received quantity of the sample has been input from the terminal device, and when it is determined that the received quantity of the sample has not been input from the terminal device, the computer uses a pre-stored value as the received quantity of the sample when calculating the dilution rate.

6. The clinical laboratory management system of claim 2, wherein the management apparatus is connected to a printing device and outputs the dilution rate to the printing device.

7. The clinical laboratory management system of claim 6, wherein the printing device prints the dilution rate and the sample identification information.

8. The clinical laboratory management system of claim 7, wherein the sample identification information is printed as a bar code.

9. The clinical laboratory management system of claim 1, wherein the management apparatus is connected to the analyzer through a network.

10. A management apparatus connected to both a first analyzer being of a type without a dilution mode for performing types of assays on a sample received in a quantity and given an analyzer specification code for identifying the analyzer and the type thereof, and a second analyzer being of a type with a dilution mode for performing types of assays on a sample received in a quantity and given an analyzer specification code for identifying the analyzer and the type thereof, comprising:
   a computer and a memory which stores (a) a database which stores the analyzer specification code and requested assay information for identifying at least one requested type of assay to be performed on the sample, and (b) a master file which stores calculation methods for calculating required total sample quantities necessary for the analyzer to perform the types of assays individually and in combination,
   the memory also storing a plurality of program modules executable by the computer to:

use the requested assay information stored in the database and one of the methods stored in the master file, which is selected by the computer in accordance with the requested assay information, to calculate, and store in the database, a required total quantity which is a minimum sample quantity necessary for one analyzer to perform the at least one requested type of assay on the sample;

receive, and store in the database, a dilution instruction for diluting the sample;

respond to reception of the dilution instruction to divide the required total quantity stored in the database by the received quantity of the sample to calculate, and store in the database, a dilution rate of the sample;

receive, and store in the database, an assay result of the sample from said one analyzer;

respond to reception of the assay result to examine the analyzer specification code of said one analyzer stored in the database and determine whether the database stores the dilution instruction, in order to decide whether said one analyzer is of a type without a dilution mode and thus the assay result should be corrected; and when it is decided that said one analyzer is of a type without a dilution mode and the assay result should be corrected, use the stored dilution rate from the database to correct the assay result with the dilution rate.

11. The management apparatus of claim 10, wherein the database stores suction quantities required for the first and second analyzers to perform the respective types of assays.

12. The management apparatus of claim 11, wherein the management apparatus is connected to a terminal device for information input, and wherein the database stores a value received from the terminal device as the received quantity of the sample.

13. The management apparatus of claim 11, wherein the received quantity of the sample is pre-stored in the database.

14. The management apparatus of claim 13, wherein the computer determines whether the received quantity of the sample has been input from the terminal device, and that when it is determined that the received quantity of the sample has not been input from the terminal device, the computer uses the pre-stored value as the quantity of the sample when calculating the dilution rate.

15. The management apparatus of claim 11, wherein the management apparatus is connected to a printing device, wherein the dilution rate is output to the printing device.

16. The management apparatus of claim 10, wherein the management apparatus is connected to the analyzer through a network.

* * * * *